United States Patent [19]

Herrero et al.

[11] Patent Number: 4,702,761
[45] Date of Patent: Oct. 27, 1987

[54] O,O-DIALKYL PHOSPHORAMIDOTHIOATE PLANT GROWTH ENHANCERS

[75] Inventors: Maria P. Herrero, Berkeley; Joseph B. Holtwick, Martinez, both of Calif.

[73] Assignee: The Dow Chemical Company, Midland, Mich.

[21] Appl. No.: 835,082

[22] Filed: Feb. 28, 1986

[51] Int. Cl.$^4$ ............................................ A01N 57/12
[52] U.S. Cl. ...................................................... 71/87
[58] Field of Search ............................................. 71/87

[56] References Cited

U.S. PATENT DOCUMENTS 3,150,039  9/1964  Lanham et al. .................... 71/87
3,511,632  5/1970  Wollensak et al. ................. 71/86
3,813,457  5/1974  Collin .............................. 260/971

OTHER PUBLICATIONS

Pellegrini et al., Chem. Abst., vol. 75, (1971), 34642z.
Fiedler et al., Chem. Abst., vol. 82, 110996e.

*Primary Examiner*—Catherine L. Mills

[57] ABSTRACT

O,O-dialkyl phosphoramidothioates, such as O,O-dimethyl phosphoramidothioate, enhance the growth of gramineous crop plants when applied to the growing plant in small quantities. The forage and ensilage yield of maize and sorghum are increased as is the grain yield of maize.

5 Claims, No Drawings

O,O-DIALKYL PHOSPHORAMIDOTHIOATE PLANT GROWTH ENHANCERS

BACKGROUND OF THE INVENTION

The desirability of enhancing the growth of crop plants and, thereby, increasing the efficiency of food and fiber production is well established. The search for methods to enhance plant growth goes back nearly to the beginning of civilization and continues to be an important endeavor. The use of chemicals other than plant nutrients to enhance plant growth is more recent, but well established in principle. Chemicals having the property of enhancing the growth of crop plants and, especially, of increasing the yield of crop plants are, therefore, valuable, and the discovery of new classes of chemicals having this property is highly desirable.

SUMMARY OF THE INVENTION

It has now been found that O,O-dialkyl phosphoramidothioates of the formula

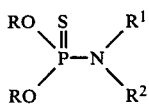

wherein
each R independently represents $C_1$–$C_4$ alkyl, and
$R^1$ and $R^2$ each independently represent hydrogen, $C_1$–$C_4$ alkyl, or $C_3$–$C_4$ alkenyl
enhance the growth of gramineous crop plants when applied to the foliage thereof in small amounts. Those compounds of the invention wherein each R independently represents methyl or ethyl are preferred and O,O-dimethyl phosphoramidothioate is especially effective.

The growth enhancement of crop plants by the O,O-dialkyl phosphoramidothioates of this invention may be exhibited in a number of ways including (a) increasing the soluble solids, such as sugars, in the stalk, (b) increasing leaf area, (c) increasing plant size, (d) increasing photosynthetic rate, and (e) increasing fruiting body production. Such growth enhancement results in an increased yield of useful product from the crop plant and other benefits. The O,O-dialkyl phosphoramidothioates of the present invention are especially potent for increasing the soluble solids in the stalks of gramineous crop plants resulting in an increased yield of forage, ensilage or sugar and for increasing the yield of grain from gramineous crop plants.

Growth enhancement following treatment by O,O-dialkyl phosphoramidothioates is exhibited by most gramineous crops including maize, grain sorghum, sweet sorghum, millet, wheat, barley, rice, sugar cane, bluegrass, timothy, and the like. Maize, grain sorghum, sweet sorghum, wheat, and sugar cane are of particular interest. Maize is especially responsive.

The treatment of plants can be made at any time between emergence and cessation of active growth, but is preferably made within 6 weeks of emergence. Treatment is usually made by applying an appropriate O,O-dialkyl phosphoramidothioate to the foliage of the plants as a dilute solution, suspension or emulsion containing chemically inert, agriculturally acceptable adjuvants or additaments. The mixture is typically applied from the ground or aerially as a spray using conventional manual or automated agricultural spray equipment.

The expression of plant growth enhancement in response to treatment by O,O-dialkyl phosphoramidothioates is dependent on the dose applied, the dose-response curves normally exhibiting a maximum at some intermediate dose. Thus, growth enhancement is not expected or found for all compounds at all application rates. Enhancement is usually exhibited when plants are treated with an amount of spray mixture containing about 1 to about 1000 ppm of an O,O-dialkyl phosphoramidothioate which results in an application rate of about 0.004 to about 4 kg/Ha. It is preferred to treat with an amount of spray mixture containing about 5 to about 500 ppm which results in an application rate of about 0.02 to about 2 kg/Ha. The concentration of the active ingredient in the spray mixture is selected to provide good coverage of the crop plants without excessive run-off when the desired dose is applied.

The optimum application rate for growth enhancement is dependent upon the O,O-dialkyl phosphoramidothioate employed, the crop treated, the stage of growth of the plant, the identity of the agricultural adjuvants employed, the climatic conditions and other factors. The determination of a suitable application rate for any specific combination of compound, crop and other factors is, however, readily achieved by those skilled in the art using routine procedures.

Dilute spray mixtures can be made directly, but it is convenient and preferred to prepare relatively concentrated formulated compositions containing O,O-dialkyl phosphoramidothioates along with one or a plurality of agriculturally acceptable adjuvants and additaments, which compositions when diluted with solvents, such as water, form the dilute solutions, suspensions, or emulsions that are applied to plants. The O,O-dialkyl phosphoramidothioate active ingredients typically constitute about 5 to about 90 weight percent of such concentrated formulated compositions. Suitable compositions may be liquid; for example, a water-soluble mixture or an emulsifiable concentrate, or solid; for example, a wettable powder or a water dispersible granule. Useful agriculturally acceptable adjuvants and additaments include chemically inert and non-phytotoxic ionic and non-ionic emulsifiers, wetting agents, dispersing agents, penetrating oils, antifoam agents, stabilizers, water, organic solvents (such as xylene, cumene, acetone, cyclohexanone, propylene glycol, butanol and kerosene), clays, silicas, and the like. A more detailed description of appropriate formulated composition ingredients and methods of preparing formulated compositions is given in U.S. Pat. No. 4,536,208 issued Aug. 20, 1985, which descriptions are hereby incorporated by reference.

The O,O-dialkyl phosphoramidothioate compounds of the present invention are well known in the art. They have been described as useful intermediates in the preparation of insecticides, herbicides and fungicides. These compounds can be readily prepared by the reaction of O,O-dialkyl phosphorochloridothioates with ammonia or an appropriate mono- or dialkylamine and can be recovered by removal of the amine hydrochloride by-product and subsequent distillation. The reaction can be illustrated as follows:

$$\underset{RO}{\overset{RO}{\diagdown}}\overset{S}{\underset{\parallel}{P}}-Cl + 2HN\underset{R^2}{\overset{R^1}{\diagdown}} \longrightarrow \underset{RO}{\overset{RO}{\diagdown}}\overset{S}{\underset{\parallel}{P}}-N\underset{R^2}{\overset{R^1}{\diagdown}} + \underset{R^2}{\overset{R^1}{\diagdown}}NH_2Cl$$

wherein R, $R^1$ and $R^2$ are as previously defined.

The following examples are presented to illustrate the invention and should not be construed as limiting.

EXAMPLE 1

Preparation of O,O-Dimethyl N,N-Diethylphosphoramidothioate $$(CH_3O)_2\overset{S}{\underset{\parallel}{P}}-N(C_2H_5)_2$$

A solution of diethylamine (7.31 g, 100 mmol) in dichloromethane (250 ml) at 5° C. was treated with O,O-dimethyl phosphorochloridothioate (8.03 g, 50 mmol) in dichloromethane (50 ml) in a dropwise fashion. The resulting mixture was stirred 1 h and then washed with 1N HCl (2X 100 ml) and water (100 ml). The dichloromethane solution was dried over magnesium sulfate and filtered, and the filtrate was concentrated under reduced pressure to give an oil. Distillation employing a Kugelrohr apparatus at 45°–50° C. and less than 1 mm Hg pressure gave 5.27 g (53 percent of theory) of the desired product; $n_D^{25}$ 1.4735.

| Analysis | C | H | N |
|---|---|---|---|
| Calcd for $C_6H_{16}NO_2PS$: | 36.54 | 8.18 | 7.10 |
| Found: | 36.30 | 8.33 | 7.06 |

EXAMPLE 2

Dry Weight Accumulation by Maize in the Greenhouse

Maize, variety Mo 17×B73, was planted in 4 inch pots filled with a soil mixture of sand, potting soil and Davis, California topsoil. The plants were allowed to grow for 2 weeks under greenhouse conditions, where they were watered with half-strength Hoagland's solution. After 2 weeks, the plants were sprayed with 1.5 ml of an aqueous mixture of an O,O-dialkyl phosphoramidothioate containing 0.1 percent TWEEN® surfactant as a wetting agent. The treated plants were maintained in the greenhouse for another 2 to 3 weeks after which time they were cut at the soil line and placed in a forced air oven at 100° C. for 36–48 hours until a stable dry weight was achieved. The dry weight accumulation was then compared to controls. The treatment rates employed and results obtained are summarized in the following table:

ENHANCEMENT OF DRY WEIGHT ACCUMULATION IN MAIZE DUE TO O,O—DIALKYL PHOSPHORAMIDOTHIOATES $$\underset{RO}{\overset{RO}{\diagdown}}\overset{S}{\underset{\parallel}{P}}-N\underset{R^2}{\overset{R^1}{\diagdown}}$$

| Compound | | | Dry Weight Percent of Control | | |
|---|---|---|---|---|---|
| R | $R^1$ | $R^2$ | 100 PPM | 10 PPM | 2.5 PPM |
| $CH_3$ | H | H | 119* | 110* | |
| $C_2H_5$ | H | H | 105 | 102 | |
| $CH_3$ | H | $CH_3$ | 110 | 104 | |
| $C_2H_5$ | H | $CH_3$ | 112 | 115 | |
| $CH_3$ | H | $C_2H_5$ | 117 | 101 | |
| $C_2H_5$ | H | $C_2H_5$ | 122 | 121 | |
| $CH_3$ | H | $C_3H_7$ | 106** | 102 | |
| $C_2H_5$ | H | $C_3H_7$ | 93 | 109 | |
| $CH_3$ | H | $i$-$C_3H_7$ | 90 | 102** | 116 |
| $C_2H_5$ | H | $i$-$C_3H_7$ | 112 | 110 | |
| $CH_3$ | H | $C_4H_9$ | 86 | 104** | 100 |
| $C_2H_5$ | H | $C_4H_9$ | | 106 | 108 |
| $CH_3$ | $CH_3$ | $CH_3$ | 88 | 97** | 109 |
| $C_2H_5$ | $CH_3$ | $CH_3$ | 119 | 120 | |
| $CH_3$ | $C_2H_5$ | $C_2H_5$ | 103** | 110** | |
| $C_2H_5$ | $C_2H_5$ | $C_2H_5$ | 107 | 119 | |
| $C_2H_5$ | $C_3H_7$ | $C_3H_7$ | 105 | 111 | |
| $CH_3$ | $C_4H_9$ | $C_4H_9$ | 94 | 103 | |
| $C_2H_5$ | $C_4H_9$ | $C_4H_9$ | 119 | 106 | |

*Average of 4 runs
**Average of 2 runs

The results shown in the table demonstrate that the O,O-dialkyl phosphoramidothioates of the invention effectively increase the dry weight accumulation of maize up to 19 percent (dry weights up to 119 percent of those of the control) at at least one application rate. At other application rates the dry weight accumulation is decreased or unchanged as would be expected for compounds having a maximum in effectiveness at an intermediate application rate.

EXAMPLE 3

Maize Yield Test

O,O-Dimethyl phosphoramidothioate was applied to maize variety NC+59 when the maize was about 6 inches tall and in the 3-4 leaf stage. A high seeding rate of maize was used to create a population stress. The phosphoramidothioate was applied at 0.5, 1.0, and 2.0 oz per acre as an aqueous spray containing 0.1 percent X-77 surfactant at the spray volume of 20 gallons per acre to test plots consisting of 2-25 foot rows. Control plots were applied in a like manner. Each treatment was replicated 5 times. At maturity the maize was harvested and the grain weighed. The yields of the control plots averaged 10.58 kg of grain per plot while the yields of the plots treated at 0.5 oz per acre averaged 12.03 kg of grain per plot. The increase of 13.7 percent is statistically significant at the 1 percent level. The yields of the plots treated at 1.0 and 2.0 oz per acre were 9.90 and 10.46 kg of grain per plot, respectively.

We claim:

1. A method of enhancing the growth of gramineous crop plants which comprises applying to the foliage of said plants a non-nutritional, growth enhancing amount of an O,O-dialkyl phosphoramidothioate compound of the formula $$\underset{RO}{\overset{RO}{\diagdown}}\overset{S}{\underset{\parallel}{P}}-N\underset{R^2}{\overset{R^1}{\diagdown}}$$

wherein
  each R independently represents $C_1$-$C_4$ alkyl, and $R^1$ and $R^2$ each independently represent hydrogen, $C_1$-$C_4$ alkyl, or $C_3$-$C_4$ alkenyl.

2. A method according to claim 1 wherein each R independently represents methyl or ethyl.

3. A method according to claim 2 wherein the compound is O,O-dimethyl phosphoramidothioate.

4. A method according to claim 1 wherein the gramineous crop plant is maize, grain sorghum, sweet sorghum, wheat or sugar cane.

5. A method according to claim 4 wherein the gramineous crop plant is maize.

* * * * *